United States Patent [19]

Pratt

[11] 4,312,769

[45] Jan. 26, 1982

[54] CONTINUOUS PROCESS FOR GREASE PREPARATION

[75] Inventor: Charles E. Pratt, Signal Mountain, Tenn.

[73] Assignee: Chattem, Inc., Chattanooga, Tenn.

[21] Appl. No.: 203,869

[22] Filed: Nov. 7, 1980

Related U.S. Application Data

[63] Continuation-in-part of Ser. No. 96,933, Nov. 23, 1979, and Ser. No. 201,272, Nov. 4, 1980, abandoned.

[51] Int. Cl.³ .......................... C10M 5/12; C10M 5/14
[52] U.S. Cl. ................................ 252/35; 252/37.7; 44/68; 260/448 R; 260/448 AD
[58] Field of Search .......................... 252/35, 37.7; 260/448 R, 448 AD; 44/68

[56] References Cited

U.S. PATENT DOCUMENTS

| | | | |
|---|---|---|---|
| 2,768,138 | 10/1956 | Hotten et al. | 252/35 |
| 3,591,505 | 7/1971 | Polishuk | 252/35 |
| 3,776,846 | 12/1973 | Bailey et al. | 252/37.7 |
| 3,791,972 | 2/1974 | Myers | 252/37.7 |
| 4,132,658 | 1/1979 | Coleman et al. | 252/37.7 |

FOREIGN PATENT DOCUMENTS 825876 12/1959 United Kingdom.

*Primary Examiner*—Jacqueline V. Howard
*Attorney, Agent, or Firm*—Hill, Van Santen, Steadman, Chiara & Simpson

[57] ABSTRACT

A continuous process for making aluminum complex greases involving the step of passing a mixed dispersion of oxyaluminum acylate and carboxylic acid material in a grease making oil through a reaction zone.

22 Claims, 2 Drawing Figures

CONTINUOUS PROCESS FOR GREASE PREPARATION

RELATED APPLICATIONS

This application is a continuation-in-part of each of my earlier filed U.S. patent applications Ser. Nos. 96,933, filed Nov. 23, 1979, and 201,272, filed Nov. 4, 1980 but now abandoned which are fully incorporated hereinto by reference.

BACKGROUND OF THE INVENTION

In the art of making aluminum complex greases, two methods of preparation were commonly employed. In one of these methods, an aluminum alkoxide is dissolved in an oil stock and two mole equivalents of an acid or acid mixture is added thereto. During subsequent heating, reaction occurred releasing one mole of alcohol per mole of acid introduced. Thereafter to the resulting system water is added which reacts with the final remaining alkoxy group thereby releasing the third and final mole of alcohol and producing a hydroxyl group on the aluminum atom. The alcohol produced is removed by distillation and, since the water is typically added in excess, the excess water is likewise removed by distillation. A typical aluminum alkoxide employed in this method is aluminum isopropoxide; see, for example U.S. Pat. No. 3,345,291 issued to Chevron Research Corporation.

In the second technique, a cyclic aluminum isopropoxide (or other alkoxide) trimer is introduced into a mineral oil. To this mixture is added a carboxylic acid mixture which is approximately equal to two moles of acid per mole of aluminum. When this mixture is heated, reaction occurs which releases one mole of alcohol per mole of aluminum. See, for example, Rinse U.S. Pat. No. 3,054,816. Apparently, it is possible to reverse the order of addition so that the cyclic aluminum isopropoxide trimer is added after the acids are introduced into the petroleum oil; see, for example, column 4 of Bailey et al U.S. Pat. No. 3,776,846. The alcohol thus produced as a by-product is removed by distillation.

Recently, I discovered that certain oxyaluminum acylates can be employed in combination with organic acids to prepare commercially greases of mineral oils in such a way as to avoid the previous problems of removing alcohol produced as a by-product in the grease manufacture and to avoid the addition and/or removal of water present in a system; see my above-identified related U.S. patent application.

Because of such previous problems with alcohol and water, it has not previously been possible to make aluminum complex greases continuously and economically without having to provide special means or techniques for removal of these materials. For example, a continuous process for making lubricating grease has been developed by Texaco, Inc.; see Green et al U.S. Pat. No. 3,475,337 and U.S. Pat. No. 3,475,335 and Witte et al in "The Texaco Continuous Grease Process" presented at the 1979 Annual Meeting of the National Lubricating Grease Institute. This process employs three sections: A reactor section, a dehydration section and a finishing section. As Witte et al state:

"Fatty material, alkali, and a diluent oil are metered into the reactor section where saponification occurs. The stream from the reactor section enters the dehydration section where the water is vaporized, leaving a dehydrated soap base. The dehydrated soap base is then mixed with additional oil and additives in the finishing section and the mixture is thoroughly homogenized, so that a uniform grease is produced."

This process requires extensive mixing in the reactor section which can lead to problems. Apparently, aluminum greases have not been commercially made by this process because of the requirements for sequential addition sections (for acid addition and water addition in the case of the aluminum alkoxide route) and because of the requirement for sequential by-product removal sections (for alcohol and for water) in the aluminum alkoxide route). By eliminating the presence of water and/or alcohol, such as can be accomplished through the use of oxyaluminum acylates in place of, for example aluminum alkoxides, process simplifications and improvements in process sections and conditions become hoped-for possibilities which could not be obtained previously.

BRIEF SUMMARY OF THE INVENTION

The present invention is more specifically directed to a new and very efficient continuous process for making aluminum complex greases which does not utilize any water-removal section or any alcohol-removal section. The process is relatively simple to operate, reliable, and economical, and overcomes the prior art problems of making continuously such aluminum greases.

By the present invention, there is thus provided a continuous process for making an aluminum complex grease wherein a sequence of steps is practiced simultaneously but sequentially. In a first step, one mixes a first dispersion of oxyaluminum acylate material with a second dispersion of carboxylic acid material in a first mixing zone to produce a substantially homogeneous product mixture. Preferably, such dispersions are true solutions.

In the next steps, one charges such product mixture into an elongated reaction zone, and then passes such product mixture through such reaction zone while maintaining said reaction zone at a temperature ranging from about 135° to 250° C. The residency time for such product mixture in such reaction zone is at least such that the oxyaluminum acylate material is substantially completely reacted with the carboxylic acid material, thereby to form a product aluminum complex grease.

Thereafter, one removes such product grease from such reaction zone, and cools same.

After a preliminary cooling, a product grease can be milled, if desired, or mixed with additional oil and additives, if desired, in one or more subsequent mixing zones.

The starting solutions can be prepared in make-up tanks, and then transferred to feed tanks, before being charged to the first mixing zone, if desired.

Other and further aims, objects, purposes, advantages, uses, and the like for the present invention will be apparent to those skilled in the art from the present specification.

DETAILED DESCRIPTION

In the process of this invention the oxyaluminum acylate material is characterized by the formula:

(1)

and by the formula (2)

wherein R is selected from the group of radicals consisting of:

Type (A): aliphatic radicals each containing from 10 to 38 carbon atoms, and

Type (B): aromatic radicals each containing from 6 to 16 carbon atoms, and wherein in any given group of such compounds, the mole percent of radicals of said Type (B) ranges from about 40 to 95 with the balance up to 100 mole percent being said Type (A) radicals.

Similarly, the carboxylic acid material is characterized by the formula:

(3)

where R' is selected from the group consisting of aliphatic radicals containing from 9 through 40 carbon atoms each and aromatic radicals containing from 6 through 28 carbon atoms each, and wherein, in any given such carboxylic acid material, the weight percent of said aromatic radicals ranges from and including 0 to about 70% with the balance up to 100 weight percent of all said radicals, being said aliphatic radicals.

The carrier liquid for each of said first and said second dispersions comprises an inert organic liquid, preferably one having a viscosity at 100° F. of from about 35 to 50,000 SUS, more preferably from about 50 to 25000 SUS, such as a hydrocarbon oil.

The total amount of aluminum in said product mixture ranges from about 0.01 to 4.0 weight percent based on total mixture weight, and preferably from about 0.01 to 2 weight percent.

The mole ratio of the total amount of aluminum to the added said carboxylic acid material ranges from about 0.75:1.25 to 1 25:0.75 in said product mixture, and preferably ranges from about 0.8:1.2 to 1.2:0.8.

One preferred class of first dispersions for use in the practice of this invention comprises on a 100 weight percent total weight basis:

(A) from about 2 to 60 weight percent of oxyaluminum acylate material as defined above, and, correspondingly (B) from about 98 to 40 weight percent of a petroleum derived hydrocarbon liquid having a viscosity at 100° F. ranging from about 35 to 50,000 SUS.

In the invention, in place of, or in combination with, such hydrocarbon liquid, one can employ any other hydrocarbonaceous liquid which would be compatible with grease systems, such as a synthetic oil, an ester of the type conventionally used or known to be compatible with synthetic lubricating oil systems, or the like. In such a first dispersion, the above indicated component (A) is uniformly dispersed in the above indicated component (B). As used herein, the term "dispersed", "dispersion", or the like is inclusive of both solutions and suspensions. Preferably, such a dispersion of this invention has the component (A) substantially completely dissolved in the component (B). Conventional methods for the preparation of such dispersions can be employed. It is noted, that the terms "component (A)" and "component (B)" used herein are different from the terms "Type (A) radicals" and "Type (B) radicals" and should not be confused with each other.

One preferred class of second dispersions for use in the practice of this invention comprises on a 100 weight percent total weight basis:

(A) from about 2 to 50 weight percent of carboxylic acid material and, correspondingly

(B) from about 50 to 98 weight percent of a petroleum derived hydrocarbon liquid having a viscosity at 100° F. ranging from about 35 to 50,000 SUS.

The process of this invention involves the converting of compounds as defined in formulas (1) and/or (2) which are dispersed (preferably dissolved) in an oil (preferably a petroleum derived hydrocarbon oil as described above) by reaction with a carboxylic acid material as defined in formula (3) into an hydroxyaluminum diacyl soap directly without the production of by-product alcohol and without water being present. The following chemical equations are illustrative of this addition reaction whereby no such by-products are formed:

Equation I where the oxyaluminum acylate compounds are represented by formula (1 )

Equation II where the oxyaluminum acylate compounds of this invention are represented by formula (2)

-continued

In equations I and II, R is as above defined, and R' is as defined above. For example, by one presently preferred procedure of this invention, to prepare a first solution or a second solution, one heats a mixture of a respective group of compounds as above defined in formulas (1), (2) or (3) with a petroleum derived hydrocarbon having a viscosity at 100° F. ranging from about 35 to 50,000 SUS (though higher and lower viscosity oils may be used if desired) until substantially all of such compounds are substantially completely dissolved in such petroleum oil. Thereafter, such resulting solution is either stored or directly used in the practice of this invention.

Any convenient method may be used to make starting solutions or dispersions for use in this invention. A principle feature of the present invention is the continuous production of smooth, clear greases in a simple and reliable manner. No precautions are needed, for example, to dissolve either the aliphatic acid or the aromatic acid used in the oil to be thickened and no special sequential addition and mixing is needed. Both the aromatic acid (e.g. benzoic acid) and the aliphatic acid (e.g. fatty acid-like stearic) can be added simultaneously as a solid powder mixture, if desired. As a convenience, it is preferred to make both dispersions above the melting point of the aliphatic acid, and more preferably in the range of 60° to 100° C., but higher and lower temperatures may be used.

Another principle feature of the present invention is that such mixed oxyaluminum acylates (as defined hereinabove) permit one to prepare continuously a grease having excellent and controllably high viscosity characteristics compared to the prior art (see, for example, Rinse U.S. Pat. No. 3,054,816).

Another feature of the present invention is that such aluminum acylates (as defined hereinabove) permit one to prepare a grease without the use of added water and without the production of any by-product alcohol or water whatsoever. The freedom from by-product alcohol formation, for example, is highly desirable both from an environmental standpoint and also from a process operational standpoint.

The preferred grease products of this invention characteristically are smooth, clear materials. They incorporate an aluminum complex soap which term, as those skilled in the art appreciate, has reference to a mixture of aluminum soap molecules containing at least one hydroxy anion for each aluminum cation and substantially two carboxylic acid anions per aluminum atom. By this invention, such an aluminum complex soap has two dissimilar acid anions, such as one aromatic (e.g. benzoate) anion, and one aliphatic (e.g. arachidate, stearate, or like fatty carboxylic acid) anion. Such an aluminum complex soap is produced by chemical reaction with the starting mixed oxyaluminum acylates with the starting carboxylic acids.

Characteristically, a controllable and uniform thickening of a starting petroleum composition mixture occurs in practicing the process of this invention.

Preferably, in formulas (1) and (2), the mole percent of said Type (B) radicals ranges from about 40 to 85 while the balance up to 100 mole percent in any given such material comprises said Type (A) radicals. Still more preferably, this mole percent of Type (B) radicals, ranges from about 45 to 80 mole percent, and even more preferably from about 45 to 75 mole percent.

As those skilled in the art will appreciate, oxyaluminum acylates of which the mixed oxyaluminum acylates of this invention, as defined above in formula (1) and (2) are believed presently to exist either in a monomeric form or in a cyclic trimeric form. The conditions under which one form exists as opposed to the other form are at this time completely unknown.

One type of preferred Type (B) radicals is derived from benzoic acid. A class of preferred oxyaluminum acylate compounds are those wherein the Type (A) radicals are derived from stearic acid or isostearic acid and wherein the Type (B) radicals are derived from benzoic acid. Another preferred class of oxyaluminum acylate compounds are those wherein the Type (A) radicals are derived from hydrogenated tallow fatty acids.

One class of preferred carboxylic acid compounds for use in this invention are derived from fish oils which contain at least about 50 percent by weight of hydrogenated fatty acids of arachidic and behenic acids, such as "Hydrofol 2022-55", available from the Ashland Chemical Company of Columbus, Ohio, USA.

Starting formula (1) and/or (2) compounds can be prepared by any convenient method including the controlled hydrolysis method and by the procedures which I have previously described in my above-referenced copending application U.S. Ser. No. 096,933 and in other copending applications filed on even date herewith.

The process of this invention is advantageously and preferably practiced with a first dispersion which additionally contains an ester material having the formula:

(4)

wherein

R is as defined above, and

R" is a lower alkyl radical, and wherein, in said first dispersion, the mole ratio of said ester material to said oxyaluminum acylate material ranges from about 1.5:1 to 0.

Further, the process of this invention is preferably and advantageously practiced by utilizing a first dispersion which additionally contains, or even comprises, an oxyaluminum acylate material which is characterized by the formula:

and by the formula (2)

wherein R''' is as R is defined above but additionally includes a further group of radicals consisting of:

Type (C): lower alkyl radicals, and wherein, in any given such oxyaluminum acylate material on a 100 mole percent total basis, the mole percent of said Type (B) radicals ranges from about 40 to 95, the mole percent of said type C radicals ranges from 0 to about 50, and the mole percent of said Type (A) radicals ranges from about 5 to 50.

Preferably, a first dispersion is prepared inherently in a process for making oxyaluminum acylates to be used in the practice of this invention.

Conveniently and preferably, each of the first dispersion and the second dispersion can be heated to temperatures which faciliate pumping, dissolution of the respective ingredients, and mixing. The respective first and second dispersions can each be pumped by a metered pump into a mixer of some desired but conventional type, such as a static mixer, a Welex-type high-intensity mixer, Prodex mixer, or the like. The mixed product stream coming from such a mixing zone then passes either directly to a reaction zone or to a heat exchange zone. If a separate heat exchange zone is employed, the temperature of the product mixture is raised to a temperature compatible with the temperatures maintainable in the reaction zone. In the reaction zone, the product mixture is heated to a temperature in the range from about 135° to 250° C. (preferably about 200° C.) in order to cause the oxyaluminum acylate material to react with the carboxylic acid material and thereby form a grease.

Observe that the process of the invention from a chemical engineering point of view is relatively simple, requiring at a minimum two feed tanks, a mixing system of some kind (perhaps a static mixer for simplicity), a long pipe or equivalent about which a heat exchange medium can be passed so as to serve as a reaction zone. The length of the tubular reaction zone is determined by the rate at which the material is pumped through the reaction zone and how long the time period is for heating the product mixture to a reaction temperature. Production capacity appears to depend upon the rate at which mixtures can be pumped through the system using available heat transfer capacity.

After passing through the reaction zone, the product grease is cooled, optionally milled in whole or in part, and optionally blended in whole or in part with various grease additives.

A present preference is to entirely cool a process grease to a lower temperature before subjecting all or a part of a product grease to a milling operation; however, if one desires to mill an entire grease, the entire product grease can be pumped through the milling zone. Conventional milling equipment may be employed. However, if one only wishes to mill a fraction of a grease product, a side stream of product grease can be diverted for the main stream, milled, and recombined with the continuously flowing main stream.

One feature of the present invention is that milling is not required for certain greases, it appears, since there is little opportunity for the continuous processing system to develop localized hot spots which, it is theorized, may well be the main cause of grease lumping. It is the phenomenon of grease lumping which has heretofore led to the desirability of milling, as those skilled in the grease making art will readily appreciate.

In addition to, or separately from, a milling zone, if desired one can also meter in and mix with a product grease various additives in appropriate mixing zones. The additives can be added to a product grease either before or after a milling operation, as those skilled in the art will appreciate. Mixing of a product grease with additives may be accomplished in a static mixer, for example, or in a continuous high intensity mixer, such as a so-called Welex or Prodex mixer. A modified extruder can be used for the mixing operation.

In the case of a tubular reactor in order to avoid irregular heating such as might occur in the region adjacent the reactor wall, a mixing of reactants in the reactor is sometimes desirable. For this purpose, a modified extruder with a suitable length and screw speed may be employed to define and operate a reaction zone. Also, the extension of the static mixer used in the mixing stage can be passed through the heat exchange area to facilitate mixing during the reaction stage.

In one presently preferred method of operating the process of the present invention, after a product grease is removed from the reaction zone, the product grease is cooled as in a heat exchanger to a temperature ranging from about 140° to 25° C. before being milled, when milling is utilized. Preferably the milling is accomplished continuously as is the cooling with the milling operation following sequentially after the cooling operation in separate respective zones. To avoid the use of a heat exchange, it may be convenient to withhold a large portion of oil needed for the finished grease and add it to the system after the aluminum containing product grease passes through the reaction zone.

In one presently preferred mode of practicing this invention, after cooling and before milling, additives are mixed with a product grease in a continuous mixing zone interposed in the system before the milling zone.

If desired, only a portion of a product grease, so cooled as above-described and so milled as above-described may be mixed with the remainder of the product grease under continuous operating conditions. Wherein cooling and milling are accomplished using only a portion of a given product grease, after the milling the portion is conveniently mixed with the remainder of a product grease in a third mixing zone. If desired, various additives may be mixed with the product grease in such third mixing zone.

For reasons of process simplicity, a present preference is to process an entire product grease by a cooling and milling operation so as to avoid side streams. If desired, after cooling and before milling, additives may be mixed with a product grease in such a second mixing zone and further additives may be mixed with such a product grease in such a third mixing zone.

In order to enhance productivity of a continuous grease making system by the practice of the present invention, the first dispersion (preferably solution) is prepared in a first make-up tank and then is transferred to a first feed tank before being fed or charged into the first mixing zone. Similarly, the second dispersion (preferably solution) is prepared in a second make-up tank and then is transferred to a second feed tank before being fed to the first mixing zone.

Conveniently, and preferably, in practicing the process of the present invention, the total amount of carrier liquid present in the first mixing zone is derived from the first dispersion and the second dispersion. A present preference is to maintain the weight ratio of carrier liquid in said first dispersion to the weight of carrier liquid in the second dispersion within a weight ratio ranging from about 80:20 to 20:80 (based upon the total weight of carrier liquid present in the first mixing zone).

Preferably in the first mixing zone, the total amount of aluminum present ranges from about 0.01 to 4.0 weight percent of the total product mixture on a 100 weight percent basis.

If desired, a plurality of first make-up tanks may be employed, and more than one first feed tank may be employed.

Figures 1, 2:
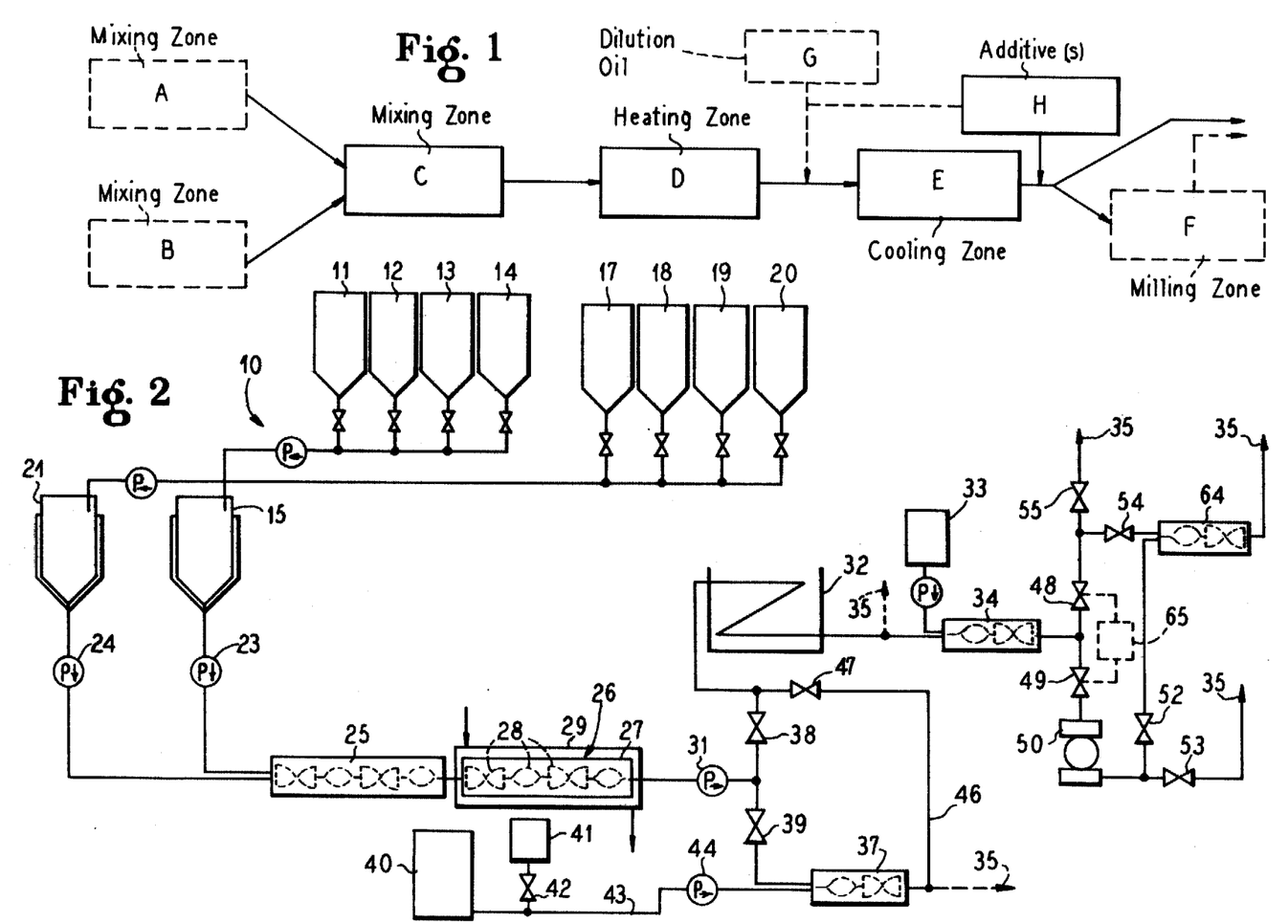
FIG. 1 is a simplified flow sheet illustrating one embodiment of the present invention.
FIG. 2 is a flow sheet illustrating a further embodiment of the present invention.

Referring to FIG. 1, there is seen a simplified flow diagram of one mode of practicing the continuous process of the present invention. In first mixing zone A, one can prepare a solution of oxyaluminum acylate of the type hereinabove defined while in a second mixing zone B one can prepare a solution of monocarboxylic acids as above defined. The solutions from the respective mixing zones A and B are then charged into another mixing zone C, in proportions so as to produce a product mixture as hereinabove defined. From the mixing zone C, the product mixture is moved into a heating zone D wherein the oxylauminum acylate material reacts with the carboxylic acid material to produce an aluminum soap as hereinabove described with the result that the material issuing from the heating zone D constitutes a grease product of the present invention.

The grease product from heating zone D, if desired, can optionally be admixed with dilution oil from a holding tank G or the like, the dilution oil and the product grease being mixed together in a mixing zone (not detailed in FIG. 1). If dilution oil is added to the product grease after heating zone D, it is preferred to charge additives into the dilution oil as such is being admixed with the product grease. Addition of additives is a common practice in the manufacture of aluminum complex greases, as those skilled in the art will appreciate, and the additives typically employed in the manufacture of aluminum complex greases are here contemplated in the amounts conventionally employed.

The product grease from heating zone D moves into a cooling zone E. The cooling zone E can be in the nature of a heat exchanger for example. Alternatively, the cooling zone E can comprise a mixing zone wherein dilution oil at ambient temperatures is admixed with the heated product grease from the heating zone D.

Following the cooling zone E, additives may be added to a product grease, the amount of cooling occurring in a cooling zone being such as to reduce the temperature of a product grease to a level above ambient where additives are conveniently mixed with a product grease, particularly when the additives involved should not be added for reasons of product stability or the like to the grease issuing from heating zone D. Typically, additives are added to a product grease issuing from cooling zone E and such additives are admixed with a product grease in a mixing zone, not detailed in FIG. 1. The product from the cooling zone, typically with additives as indicated, can then be moved into a storage area, containerized, or the like, as desired, and as those skilled in the art will appreciate. Alternatively, the product from cooling zone E can be moved into a milling zone so as to mill a product grease to some predetermined desired extent, all in the manner conventionally accomplished in the manufacture of aluminum complex greases. If milling is accomplished, the product from the milling zone can be moved into storage, container loading, or the like, as desired. Any convenient or desired technique for processing a product grease from a cooling zone E can be utilized, as those skilled in the art will appreciate, without departing from the spirit and scope of the present invention.

Referring to FIG. 2, there is seen a simplified schematic view of one embodiment of a commercial scale operation utilizing the continuous grease making process of the present invention, such operation, for convenience, being designated in its entirety herein by the numeral 10. Operation 10 is seen to employ a plurality of first make-up tanks designated herein as 11, 12, 13 and 14, respectively, such tanks 11–14 being adapted for the preparation of starting dispersions of oxyaluminum acylates in accordance with the practice of the present invention. In each make-up tank, an oxyaluminum acylate/base oil solution, for example, is made-up. Each solution is conveniently analyzed for percent aluminum metal and any adjustments in solution components necessary to achieve a standardized prechosen composition are made. After which, preferably in a sequence, the contents of each make-up tank 11-14 is charged into a feed tank 15.

Similarly, a plurality of make-up tanks 17, 18, 19 and 20 are provided in which, respectively, solutions of, for example, stearic acid, benzoic acid and base oil are made-up. Each acid solution is tested as by an acid number titration to determine the acid content of that tank. After any adjustments for accuracy or the like are made, the contents of a respective tank 17–20 are charged into a feed tank 21. The respective contents of feed tanks 15 and 21 may be preheated, if desired, to some prechosen temperature in order facilitate subsequent mixing. The contents of the respective tanks 15 and 21 are charged via metering pumps such as pumps 23 and 24 into a mixing zone 25. The mixing zone 25 is here shown as a static mixer which is a particularly convenient and presently preferred unit for accomplishing mixing of materials from feed tanks 15 and 21. A product mixture from the mixing zone (static mixer) 25 is continuously moved into a reaction zone 26. Zone 26 is here comprised of an elongated tube 27, wherein static mixer vanes 28 are positioned. In addition, the tube 27 is provided with a heating mantle or jacket through which heating fluid (such as heated oil or a vaporized heat exchange material, such as the type available commercially under the trademark "DOWTHERM" from Dow Chemical Company, Midland Michigan, is circulated. Thus, as a product mixture moves continuously through the tube 27, it is continuously mixed so as to prevent localized overheating or underheating of a given location from occurring. The jacket temperature on tube 27 and the length of tube 27 are so regulated and chosen that by the time material issues from the tube 27, a substantially complete reaction has taken place between the oxyaluminum acylate material and the carboxylic acid material present, so that the product issuing from the tube 27 constitutes a product grease of this invention.

Although not shown in FIG. 2, as chemical engineers will appreciate, it may be advisable to place a holding tank, or the like, after the reaction zone 26 in order to provide for flow variations or the like in the continuous process stream involved.

The product from the reaction zone 26 is moved by a pump 31, if desired, into a heat exchange zone 32, so as to controllably cool the product grease to some predetermined lower temperature, after which the so-cooled product grease can be admixed with additives from hold tank 33, the additives being charged along with the so-cooled grease into a mixing zone 34, such mixing zone 34 being conveniently a static mixer or the like, as those skilled in the art will appreciate. The product from mixing zone 35, if desired, can then be directly moved towards a storage area 35 or the like (not detailed herein but conventional).

Alternatively, instead of the procedure above related, a product from the reaction zone 26 can be moved into a mixing zone 37 by appropriate settings for valves 38 and 39. In mixing zone 37, a product grease can be diluted with a dilutant oil from a reservoir tank 40. To the dilutant oil 40 can be added additives, if desired, from a holding tank 41, the tank 41 being conveniently provided with a valve 42 for regulating flow of additives from tank 41 into oil from reservoir 40 in feed line 43. The flow through line 43 is conveniently regulated into the mixing zone 37 by a metering pump 44. From the mixing zone 37 the product mixed diluted grease is led through pipe 46 passed open valve 47 into the heat exchanger 32, wherein the product mixture may be reduced to some lower prechosen temperature, which is lower than the temperature produced in the mixed diluted grease as a result of mixing with the product grease the ambient temperature dilutant oil. As those skilled in the art will appreciate, it is possible that the product from the mixing zone 37 is cool enough for immediate discharge from the mixing zone 37 to a storage area 35. If further cooling and heat exchanger 32 is desirable or necessary, the diluted product grease from exchanger 32 can be directly diverted to the storage area 35, if desired.

If desired, a product grease produced by the process of the present invention can be subjected to a milling operation of the type conventionally utilized in the aluminum complex grease making art. For example, a product grease stream leaving mixing zone 34 can be diverted using valves 48 and 49 in proper sequence into a milling zone 50, after which the discharge from the milling zone 50 is either moved directly to a storage area 35 or (by, for example, regulating an appropriate valve network comprised, for example) a valve such as 52 and 53 into a further mixing zone 64 wherein the milled grease can be continuously recombined with product grease which is unmilled and which is derived from the product stream produced from the mixing zone 34 (assuming an appropriate configuration for valves 48 and 54, for example). In order to obtain a proper ratio of milled grease to unmilled grease, an appropriate ratio flow control 65 could be employed, in the embodiment shown, for valves 48 and 49, as those skilled in the art will appreciate. In such a blending of milled with unmilled grease, the valves 53 and 55 would be closed, and the product from the mixing zone 64 would be moved into a storage 35.

EMBODIMENTS

The present invention is further illustrated by reference to the following Examples. Those skilled in the art will appreciate that other and further embodiments are obvious and within the spirit and scope of this invention from the teachings of these present Examples taken with the accompanying specification.

EXAMPLE A

An oxyaluminum acylate composition suitable for use in the practice of the process of the present invention is prepared as follows:

To a 22 liter 3-neck flask is added the following ingredients 4,998.6 grams hydrogenated tallow fatty acid, 2,197.8 grams benzoic acid and 3,816 grams ispropanol. This mixture is heated to approximately 60° C. at which point the mixture is a clear low viscosity homogenous liquid. To this mixture is then added 3,675.6 grams granulated aluminum isopropylate. Heat is applied to the flask and the temperature gradually raised to the point where isopropanol begins to distill off. As the distillation continues temperature readings are taken at 60 minute intervals and the following Table results:

TABLE I

| Pot Temperature | Vapor Temperature |
| --- | --- |
| 84° C. | 81° C. |
| 85° C. | 81° C. |
| 85° C. | 81° C. |
| 85° C. | 81° C. |
| 93° C. | 81° C. |
| 100° C. | 81° C. |
| 120° C. | 81° C. |
| 166° C. | 84° C. |

At this point, the heating causes the temperature to begin rising much more rapidly and it reaches 200° C. within another hour. During the time of the first and second steps of heating, both the added isopropyl alcohol and 2 moles of produced isopropyl alcohol on a theoretical basis are removed from the flask. The temperature is then maintained at 200° C. for one more hour after which it is allowed to cool. The product is a light amber clear liquid which is analyzed to be 5.67% aluminum and by further analysis it is determined that the oxyaluminum acylate so produced contains 75.3% benzoic radicals. The oxyaluminum acylate is dissolved in a mixture of isopropyl benzoate and isopropyl hydrogenated tallowate.

EXAMPLE B

A carboxylic acid mixture suitable for use in the practice of the present invention is prepared as follows:

Into a 15 gallon epoxy lined drum is charged 50.6 pounds of a grease base oil having a viscosity at 100° F. of no more than about 1800 SUS. This drum is provided with an impeller driven by an electric motor and also with an external electric heating device to heat the contents to a predetermined temperature. The oil is agitated and raised to a temperature of about 90° C. after which is added 4.75 pounds of hydrogenated tallow fatty acid and 0.25 pounds benzoic acid.

EXAMPLE C

An oxyaluminum acylate composition suitable for use in the practice of the present invention is prepared as follows:

To a 22 liter 3-neck flask is added the following ingredients: 4,499 grams hydrogenated tallow fatty acid, 2,418 grams benzoic acid and 3,672 grams isopropanol. This mixture is heated to approximately 60° C. at which point the mixture is a clear low viscosity homogenous liquid. To this mixture is then added 3,675.6 grams granulated aluminum isopropylate. Heat is applied to the flask and temperature gradually raised to the point where isopropanol begins to distill off. As the distillation continues periodic temperature readings are taken and the following Table results:

TABLE II

| Hours | Pot Temperature | Vapor Temperature |
|---|---|---|
| 0 | 84° C. | 81° C. |
| 2 | 84° C. | 81° C. |
| 2.5 | 91° C. | 81° C. |
| 3 | 95° C. | 81° C. |
| 6.5 | 100° C. | 80° C. |
| 7.5 | 170° C. | 80° C. |
| 8 | 201° C. | 33° C. |
| 9.5 | 207° C. | 33° C. |

During the heating, both the added isopropyl alcohol and 2 moles of produced isopropyl alcohol on a theoretical basis are removed from the flask. The flask is then allowed to cool. The product is a light amber clear liquid which is analyzed to be 5.96% aluminum and by further analysis it is determined that the oxyaluminum acylate so produced contained 81% benzoic radicals. The oxyaluminum acylate is dissolved in a mixture of isopropyl benzoate and isopropyl hydrogenated tallowate.

EXAMPLE D

A carboxylic acid mixture suitable for use in the practice of the present invention is prepared as follows:

To a similarly equipped drum as used in Example B is charged 50.75 pounds of the same grease base oil as identified in Example B. The oil is agitated and heated to a temperature of about 90° C. after which is added 5.2 pounds of hydrogenated tallow fatty acids and 0.15 pounds benzoic acid.

EXAMPLE E

A carboxylic acid mixture suitable for use in the practice of the present invention is prepared as follows:

To a similarly equipped drum as used in Examples B and D is charged 50.75 pounds of the same grease base oil as used in Example B. The oil is agitated and heated to a temperature of about 90° C. after which is added 6.0 pounds of hydrogenated tallow fatty acids.

EXAMPLE F

An oxyaluminum acylate composition suitable for use in the practice of the present invention is prepared as follows:

To a 22 liter 3-neck flask is added 2,332 grams Coray 22 oil (lubricating base oil having an approximate viscosity of 100 SUS at 100° F.). To this oil in such a flask is added the following ingredients: 1,320 grams acetic acid, 2,996 grams hydrogenated tallow fatty acids, 1,342 grams benzoic acid. This mixture is warmed slightly to produce a homogenous clear liquid. The temperature is then raised to 65° C. and at this point is added to the system 4,492 grams aluminum isopropylate. This mixture is stirred and the temperature gradually increased to a point where isopropanol begins to distill off. As the distillation continues periodic temperature readings are taken and the following Table results:

TABLE III

| Time | Pot Temperature | Vapor Temperature |
|---|---|---|
| 0 | 90° C. | 82° C. |
| 1.0 | 90° C. | 82° C. |
| 1.5 | 92° C. | 82° C. |
| 2.5 | 97° C. | 82° C. |
| 3.0 | 106° C. | 82° C. |
| 4.0 | 135° C. | 84° C. |
| 4.5 | 160° C. | 96° C. |
| 5.5 | 185° C. | 108° C. |
| 6.0 | 195° C. | 94° C. |
| 6.5 | 210° C. | 115° C. |
| 7.0 | 215° C. | 115° C. |
| 7.5 | 218° C. | 112° C. |

After seven and one half hours of total elapsed time, the heat was turned off and an additional 2,332 grams Coray 22 base oil were added to the flask. During the distillation a total of 2 moles isopropyl alcohol are removed after which 1 mole of isopropyl acetate is removed all on a theoretical basis. The reaction mixture is thereafter allowed to cool to room temperature. The product is a clear high viscosity amber liquid which is found by analysis to contain 5.77% aluminum indicating approximately 50% solution (in 100 SUS 100° F. lubricating oil) of mixed oxyaluminum stearate/benzoate wherein the mole percent benzoate is 50%.

CONTINUOUS PROCESS

EXAMPLE 1

Into a 15 gallon epoxy lined drum is charged 50.6 pounds of a grease base oil having a viscosity at 100° F. of no more than 1800 SUS. This drum is provided with an impeller driven by an electric motor and also with an external electric heating device to heat the contents to a predetermined temperature. The oil is agitated and raised to a temperature of about 90° C. after which is added 10.25 pounds of an oxyaluminum acylate intermediate composition prepared as described in Example A (above). The entire resulting mixture is brought to a temperature estimated to be about 90° C., and mixing is continued until a homogenous clear solution is obtained, wherein the total weight percentage of mixed oxyaluminum acylate is estimated to be about 7.0 weight percent. The total weight percent of high boiling isopropanol mixed acid esters is estimated to be about 9.7 weight percent, with the balance up to 100 weight percent being the grease base oils as described above.

The drum containing the oxyaluminum acylate solution described above and the drum containing the acid solution as described in Example B are both connected by suitable piping to a Kenics standard static mixer, (which has an internal diameter of ⅜" and contains 21 elements) through metering pumps. The static mixer is in turn interconnected through a surge tank/booster pump combination device with a coiled copper tube, approximately 8 feet in length and having an internal diameter of about ⅜ inches. This coiled tubing is imersed in a drum of heat exchange oil which has been heated to a temperature sufficient to maintain the interior of the coiled tubing at a temperature of not less than 200° C. The discharge end of the reactor coil is placed over a 15 gallon receiving drum which is equipped with a cooling coil through which water is circulated.

The contents of the first drum are charged into the feed end of the static mixer at a rate estimated to be about 0.125 gallons per minute while the contents of the second drum are similarly charged at rate estimated to be about 0.125 gallons per minute. Thus, the total amount of aluminum in the combined mixture entering the static mixer is calculated to be about 0.5 weight percent (based upon total composition in the static mixer). Also, in the static mixer, the mole ratio of the total amount of aluminum to total carboxylic acid material is calculated to be about 1:1.92, the total carboxylic acid material here defined as the acids added from the second drum combined with the acylate groups present as part of the oxyaluminum acylate composition. The effluent from the static mixer is believed to be homogenous and uniform in composition. After passing through the surge tank/booster pump device, the flow rate of the combined mixture entering the tube reactor is estimated to be about 0.25 gallons/min. The temperature of the material being discharged from the reactor is estimated to be about 200° C. The product from the tubular reactor is discharge into the receiving container and cooled to a lower temperature by the cooling coils. The product is a clear grease having a dropping point estimated to be higher than 475° F. and an unworked penetration estimated to be less than 300.

EXAMPLE 2

Into a 15 gallon epoxy lined drum is charged 50.75 pounds of a grease base oil having a viscosity of 100° F. of no more than 1800 SUS. This drum is provided with an impeller driven by an electric motor and also with an external electric heating device to heat the contents to a predetermined temperature. The oil is agitated and raised to a temperature of about 90° C. after which is added 9.8 pounds of an oxyaluminum acylate intermediate composition prepared as described in Example C (above). The entire resulting mixture is brought to a temperature estimated to be about 90° C., and mixing is continued until a homogenous clear solution is obtained, wherein the total weight percentage of mixed oxyaluminum acylate is estimated to be about 6.7 weight percent, the total weight percent of high boiling isopropanol mixed acid esters is estimated to be about 9.5 weight percent, with the balance up to 100 weight percent being the grease base oil as described above.

The drum containing the oxyaluminum acylate solution described above and the drum containing the acid solution as described in Example D are both fed into the same equipment as described in Example 1.

The contents of the first drum are charged into the feed end of the static mixer at a rate estimated to be about 0.125 gallons per minute while the contents of the second drum are similarly charged at a rate estimated to be about 0.125 gallons per minute. Thus, the total amount of aluminum in the combined mixture entering the static mixer is calculated to be about 0.5 weight percent (based upon total composition in the static mixer). Also, in the static mixer, the mole ratio of the total amount of aluminum to total carboxylic acid material is calculated to be about 1:1.92, the total carboxylic acid material here defined as the acids added from the second drum combined with the acylate groups present as part of the oxyaluminum acylate composition. The effluent from the static mixture is believed to be homogenous and uniform in composition. After passing through the surge tank/booster pump device, the flow rate of the combined mixture entering the tube reactor is estimated to be about 0.25 gallons/min. The temperature of the material being discharged from the reactor is estimated to be about 200° C. The product from the tubular reactor is discharged into the receiving container and cooled to a lower temperature by the cooling coils. The product is a clear grease having a dropping point estimated to be higher than 475° F. and an unworked penetration estimated to be less than 300.

EXAMPLE 3

Into a 15 gallon epoxy lined drum is charged 50.75 pounds of a grease base oil having a viscosity at 100° F. of no more than 1800 SUS. This drum is provided with an impeller driven by an electric motor and also with an external electric heating device to heat the contents to a predetermined temperature. The oil is agitated and raised to a temperature of about 90° C. after which is added 9.8 pounds of an oxyaluminum acylate intermediate composition prepared as described in Example C (above). The entire resulting mixture is brought to a temperature estimated to be about 90° C., and mixing is continued until homogenous clear solution is obtained, wherein the total weight percentage of mixed oxyaluminum acylate is estimated to be about 6.7 weight percent, the total weight percent of high boiling isopropanol mixed acid esters is estimated to be about 9.5 weight percent with the balance up to 100 weight percent being the grease base oil as described above.

The drum containing the oxyaluminum acylate solution described above and the drum containing the acid solution as described in Example E are both fed into the same equipment as described in Example 1.

The contents of the first drum are charged into the feed end of the static mixer at a rate estimated to be about 0.125 gallons per minute while the contents of the second drum are similarly charged at a rate estimated to be about 0.125 gallons per minute. Thus, the total amount of aluminum in the combined mixture entering the static mixer is calculated to be about 0.5 weight percent (based upon total composition in the static mixer). Also, in the static mixer, the mole ratio of the total amount of aluminum to total carboxylic acid material is calculated to be about 1:2, the total carboxylic acid material here defined as the acids added from the second drum combined with the acylate groups present as part of the oxyaluminum acylate composition. The effluent from the static mixture is believed to be homogenous and uniform in composition. After passing through the surge tank/booster pump device, the flow rate of the combined mixture entering the tube reactor is estimated to be about 0.25 gallons per minute. The temperature of the material being discharged from the reactor is estimated to be about 200° C. The product from the tubular reactor is discharged into the receiving container and cooled to a lower temperature by the cooling coils. The product is a clear grease having a dropping point estimated to be higher than 475° F., and an unworked penetration estimated to be less than 300.

EXAMPLE 4

Into a 15 gallon epoxy lined drum is charged 51.2 pounds of a grease base oil having a viscosity at 100° F. of no more than 1800 SUS. This drum is provided with an impeller driven by an electric motor and also with an external electric heating device to heat the contents to a predetermined temperature. The oil is agitated and raised to a temperature of about 90° C. after which is added 10.1 pounds of an oxyaluminum acylate intermediate composition prepared as described in Example F (above). The entire resulting mixture is brought to a temperature estimated to be about 90° C., and mixing is continued until a homogenous clear solution is obtained, wherein the total weight percentage of mixed oxyaluminum acylate is estimated to be about 8.2 weight percent, with the balance up to 100 weight percent being grease base oil.

The drum containing the oxyaluminum acylate solution described above and the drum containing the acid solution as described in Example G are both connected to the same equipment as described in Example 1.

The contents of the first drum are charged into the feed end of the static mixer at a rate estimated to be about 0.125 gallons per minute while the contents of the second drum are similarly charged at a rate estimated to be about 0.125 gallons per minute. Thus, the total amount of aluminum in the combined mixture entering the static mixer is calculated to be about 0.5 weight percent (based upon total composition in the static mixer). Also, in the static mixer, the mole ratio of the total amount of aluminum to total carboxylic acid material is calculated to be about 1:1.92, the total carboxylic acid material here defined as the acids added from the second drum combined with the acylate groups present as part of the oxyaluminum acylate composition. The effluent from the static mixer is believed to be homogenous and uniform in composition. After passing through the surge tank/booster pump device, the flow rate of the combined mixture entering the tube reactor is estimated to be about 0.25 gallons per minute. The temperature of the material being discharged from the reactor is estimated to be about 200° C. The product from the tubular reactor is discharged into the receiving container and cooled to a lower temperature by the cooling coils. The product is a clear grease having a dropping point estimated to be higher than 475° F., and an unworked penetration estimated to be less than 300.

As those skilled in the art will appreciate, minor amounts of various carboxylic acids known to the art of grease making can be present, if desired, in the reactants employed to make a grease as described herein.

EXAMPLE G

A carboxylic acid mixture suitable for use in the practice of the present invention as prepared as follows: To a similarly equipped drum as used in Example B, is charged 51.2 pounds of the same grease base oil as is identified in Example B. The oil is agitated and heated to a temperature of about 90° centigrade after which is added 3.3 pounds of hydrogenated tallow fatty acids and 0.9 pounds benzoic acid.

I claim:

1. A continuous process for making an aluminum complex grease comprising the steps of simultaneously but sequentially:
   (A) mixing a first dispersion of oxyaluminum acylate material with a second dispersion of carboxylic acid material in a first mixing zone to produce a substantially homogeneous product mixture,
      (1) said oxyaluminum acylate material being characterized by the formula:

and by the formula wherein R is selected from the group of radicals consisting of:
   Type (A): aliphatical radicals each containing from 10 to 38 carbon atoms, and
   Type (B): aromatic radicals each containing from 6 to 16 carbon atoms, and
wherein, in any given such oxyaluminum acylate material, the mole percent of the number of radicals of said Type (B) radicals ranges from about 40 to 95 with the balance up to 100 mole percent being said Type (A) radicals,
      (2) said carboxylic acid material being characterized by the formula:

where R' is selected from the group consisting of aliphatic radicals containing from 9 through 40 carbon atoms each and aromatic radicals containing from 6 through 28 carbon atoms each, and wherein in any given such carboxylic acid material the weight percent of said aromatic radicals ranges from and including 0 to about 70% with the balance up to 100 weight percent of all said radicals being said aliphatic radicals,
      (3) the carrier liquid for each of said first and said second dispersions comprising an inert organic liquid having a viscosity at 100° F. of from about 35 to 50,000 SUS,
      (4) the total amount of aluminum in said product mixture ranging from about 0.01 to 2.0 weight percent based on total mixture weight, and
      (5) the mole ratio of said total amount of aluminum to added said carboxylic acid material ranging from about 0.75:1.25 to 1.25:0.75,
   (B) charging said product mixture into an elongated reaction zone,
   (C) passing said product mixture through said reaction zone while maintaining said reaction zone at a temperature ranging from about 135° to 250° C., the residency time for said product mixture in said reaction zone being at least such that said oxyaluminum acylate substantially completely reacts with said carboxylic acid, thereby to form a product aluminum complex grease,
   (D) removing said product grease from said reaction zone, and
   (E) cooling said product grease.

2. The process of claim 1 wherein said first dispersion additionally contains an ester material having the formula wherein R is as defined in claim 1 and R" comprises a lower alkyl radical, and wherein, in said first dispersion, the mole ratio of said ester material to said oxyaluminum acylate material ranges from about 1.5:1 to 0.

3. The process of claim 1 wherein, after said removing, at least a portion of said product grease is cooled to a temperature ranging from about 140° to 25° C. and then is milled.

4. The process of claim 3 wherein said cooling and said milling are accomplished continuously and in sequence in separate respective zones.

5. The process of claim 1 wherein said first dispersion additionally contains a second oxyaluminum acylate material which is characterized by the formula:

and by the formula wherein R''' is as R is defined in claim 1 but additionally includes a further groups of radicals consisting of:
Type (C): lower alkyl radicals, and
wherein, in any given such oxyaluminum acylate material on a 100 mole percent total basis, the mole percent of said Type B radicals ranges from about 40 to 95, the mole percent of said Type (C) radicals ranges from 0 to about 50, and the mole percent of said Type (A) radicals ranges from about 5 to 50.

6. The process of claim 4 wherein after said cooling, additives are mixed with grease before said milling in a second mixing zone.

7. The process of claim 3 wherein a portion of said product grease is so cooled and so milled and then is mixed with the remainder of said product grease.

8. The process of claim 4 wherein said cooling and said milling are accomplished using a portion of said product grease, and after said milling said portion is mixed with the remainder of said product grease in a third mixing zone.

9. The process of claim 8 wherein additives are mixed with said product grease in said third mixing zone.

10. The process of claim 4 wherein all of said product grease is so cooled and so milled.

11. The process of claim 10 wherein after said cooling before said milling additives are mixed with said grease in a second mixing zone.

12. The process of claim 10 wherein after said milling additives are mixed with said grease in a third mixing zone.

13. The process of claim 1 wherein said first dispersion is prepared in a first make-up tank and then is first transferred to a first feed tank before being fed to said first mixing zone.

14. The process of claim 1 wherein said second dispersion is prepared in a second make-up tank and then is secondly transferred to a second feed tank before being fed to said first mixing zone.

15. The process of claim 1 wherein the total amount of said carrier liquid is divided between said first dispersion and said second dispersion in a weight ratio ranging from about 80:20 to 20:80 based upon the total weight of said carrier liquid in said first mixing zone.

16. The process of claim 1 wherein said first mixing zone, the total amount of aluminum present ranges from about 0.01 to 4 weight percent of the total product mixture on a 100 weight percent basis.

17. The process of claim 13 wherein before said first transferring said first solution is analyzed for weight percent aluminum based on total first solution and such weight percent corresponds to the total quantity of aluminum desired in said product mixture.

18. The process of claim 14 wherein before said second transferring said second solution is titrated to determine the acid number thereof and such acid number corresponds to the total quantity of said carboxylic acid desired in said product mixture.

19. The process of claim 1 wherein, before said cooling, said product grease is mixed with a hydrocarbonaceous liquid in a separate mixing zone.

20. The process of claim 1 wherein said first dispersion is added from at least two separate feed streams into said first mixing zone.

21. The process of claim 1 wherein said second dispersion is added from at least two separate feed streams into said first mixing zone.

22. The process of claim 1 wherein an additional predetermined quantity of said carrier liquid is added into said first mixing zone.

* * * * *